United States Patent
Soldner

[11] 4,029,084
[45] June 14, 1977

[54] ULTRASOUND APPLICATOR WITH GUIDE SLOT FOR PUNCTURING CANNULA

[75] Inventor: Richard Soldner, Erlangen, Germany

[73] Assignee: Siemens Aktiengesellschaft, Berlin & Munich, Germany

[22] Filed: Dec. 9, 1975

[21] Appl. No.: 639,170

[30] Foreign Application Priority Data

Dec. 23, 1974 Germany .................. 7442924[U]

[52] U.S. Cl. ............................. 128/2 V; 73/67.8 R
[51] Int. Cl.² ........................................ A61B 10/00
[58] Field of Search .......... 128/2 V, 2.05 Z, 303.1, 128/303.19; 73/67.8

[56] References Cited
UNITED STATES PATENTS

| | | | |
|---|---|---|---|
| 2,697,433 | 12/1954 | Zehnder .................. | 128/303.1 X |
| 3,556,079 | 1/1971 | Omizo .................. | 128/2 V |
| 3,577,772 | 5/1971 | Perilhou .................. | 73/67.7 |
| 3,721,227 | 3/1973 | Larson et al. .................. | 128/2 V |
| 3,789,833 | 2/1974 | Bom .................. | 128/2 V |
| 3,881,466 | 5/1975 | Wilcox .................. | 128/2 V |

*Primary Examiner*—Kyle L. Howell
*Attorney, Agent, or Firm*—Hill, Gross, Simpson, Van Santen, Steadman, Chiara & Simpson

[57] ABSTRACT

An ultrasound applicator for ultrasonic-echo planigraphic imaging apparatus, consisting of a plurality of ultrasound transducer elements which are located on the application surface of a carrier portion in at least one row adjacent to each other. The carrier portion is provided with a guide slot for the puncturing cannula which extends across the transducer row along the longitudinal direction thereof, and which reduces from a predetermined maximum slot length at the surface remote from the application surface of the carrier portion to a minimum slot length at the application surface.

12 Claims, 2 Drawing Figures

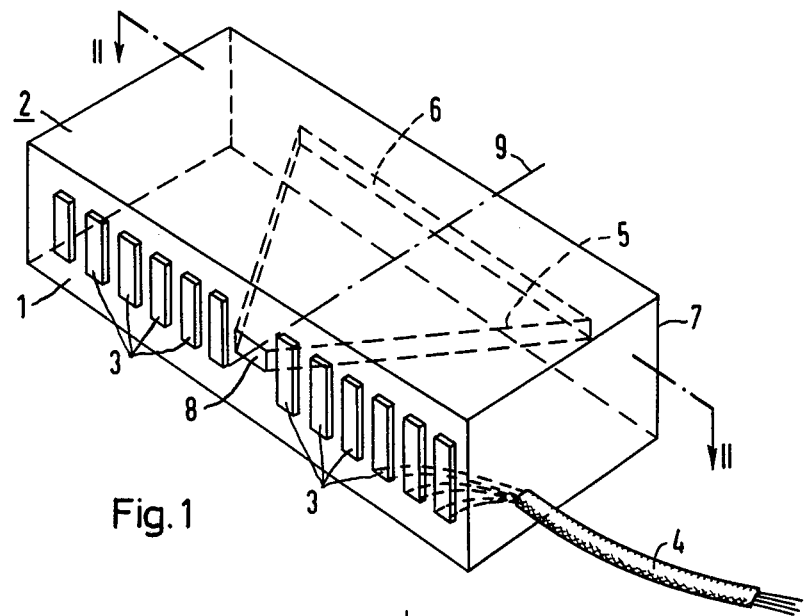
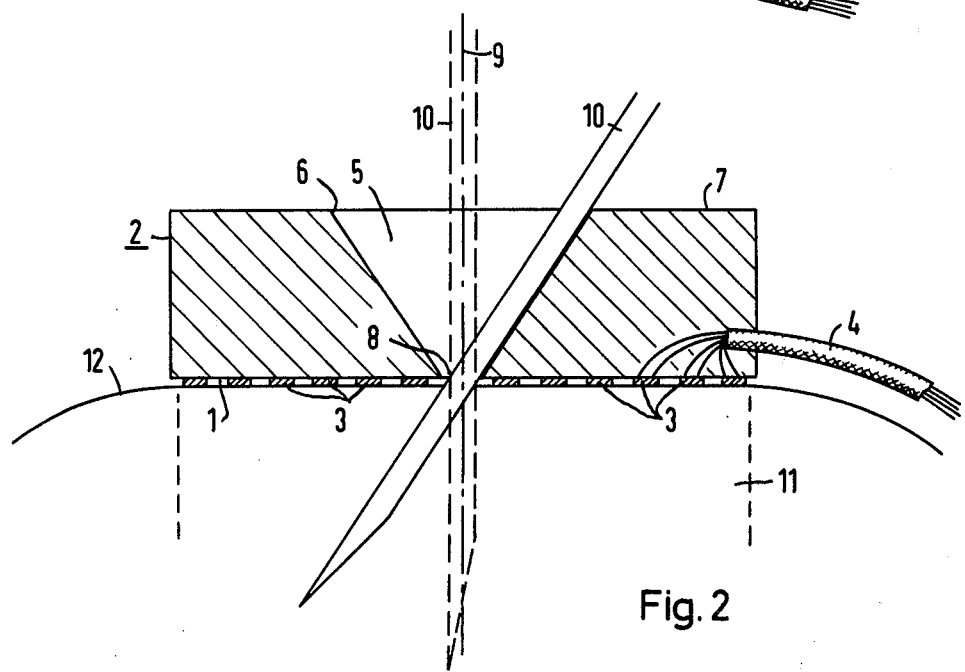

ULTRASOUND APPLICATOR WITH GUIDE SLOT FOR PUNCTURING CANNULA

FIELD OF THE INVENTION

The present invention relates to an ultrasound applicator for ultrasonic-echo planigraphic imaging apparatus, consisting of a plurality of ultrasound transducer elements which are located on the application surface of a carrier portion in at least one row adjacent to each other.

DISCUSSION OF THE PRIOR ART

It is known that, by means of suitable puncturing cannulas or needles, tissue or body fluids may be withdrawn for diagnostic purposes from internal body organs, for example, from the liver or kidneys. Similarly, for example, during a pregnancy there may be withdrawn for the same purpose amniotic fluid from the uterus or, for instance, blood or a medication may be injected into the fetal body.

In all of these instances it is of extraordinary importance that there be known the exact position of the puncturing cannula with regard to the organ or vessel which is to be punctured so as to prevent unnecessary injuries to endangered areas, for example, the placenta during puncturation of the uterus or, for example, to also avoid an erroneous tissue withdrawal from the undesired body areas, or to avoid faulty injecting during an injection.

Known ultrasound applicators of the above-mentioned type, in conjunction with ultrasonic-echo planigraphic imaging apparatus, facilitate the continual puncturing control through the assistance of ultasound, in particular with the rapid ultrasound-planigraphic image recording pursant to the B-scan procedure. Hereby, through the rapid sequential activation of the individual ultrasound transducer elements located on the applicator, the body region which is to be punctured is rapidly linewise scanned in a sectional plane by means of the ultrasonic beam and, upon the reproduction of the ultrasonic-echo impulses on the picture screen of a viewing apparatus, there is thus selected a sectional image plane which is preferred for the puncturing aiming direction. The puncturing cannula or needle which is conducted within the plane is similarly readily visible on the picture screen, since the cannula material (for example, a metal cannula) is in a good distinguishable ultrasound contrast to the surrounding biological tissue.

However, not withstanding good viewing control within the scanning region there are nevertheless still encountered aiming problems. Thus, the movement of the cannula within the tissue can be directly followed by the eye on the picture screen of the viewing apparatus, but only at the time when the cannula actually comes into the region of the ultrasonic-scanning waves in the scanning sectional plane. However, until reaching the targeted or aimed at scanning area, the injecting procedure is carried out blind; the injection of the cannula must consequently be corrected more or less frequently in accordance with the skill of the personnel effectuating the puncturing. Frequent corrections in the inserting direction of the puncturing cannula lead, however, to undesired tissue injuries and, in general delay the puncturing procedure.

SUMMARY OF THE INVENTION

Accordingly, it is an object of the present invention to provide, in an ultrasound applicator of the above-mentioned type, means which permit for the well-aimed introduction of the puncturing cannula or into the body region which is to be punctured which is essentially independent of the skill of the particular operating personnel.

The foregoing object is inventively attained in that the carrier portion is provided with a guide slot for the puncturing cannula which extends across the transducer row along the longitudinal direction thereof, and which reduces from a predetermined maximum slot length at the surface remote from the application surface of the carrier portion to a minimum slot length at the application surface.

A guide slot which is so located and formed in this manner the carrier portion facilitates the aimed insertion or infeed of a puncturing cannula, from a suitably selectable perpendicular or inclined position within known boundaries, directly into the examination area which is being traversed by the ultrasound beam. On the one hand, the cannula is hereby immediately rendered visible together with the injection on the picture screen of the viewing apparatus, so as to initially preclude the necessity of blind aiming. On the other hand, due to the possible pivoting of the puncturing cannula from the vertical into a suitable inclined position within their boundaries, the reducing guide slot allows the targeting or aiming of suitable puncturing points within a known depth region of the body below the ultrasound applicator. Since the slot appreciably reduces towards the application surface of the carrier portion (preferably, the minimum slot length at the application surface should not be substantially larger than that of the obtained oblique cross-section of an optimally thick punturing cannula at the maximum oblique position of the cannula), the cannula is well supported in the slot aperture on the application side in each inclined position thereof whereby there is afforded optimum aiming assurance at an at most minor after-adjustment. Under circumstances, the punctuation may thereby also be effectuated by less practiced aides.

Ultrasound applicators with a guide bore for a puncturing cannula have namely been known for a considerable period of time from the Ultrasound-Doppler blood flow measuring technique. In those types of guide bores, however, as distinquished from the present invention, there is dealt with concentric circular bores in the carrier portion for a single ultrasound oscillator. The circular bore, whose diameter is selected so as to be only slightly larger than the diameter of the puncturing cannula which is to be presently employed merely serves to prevent deviation of the cannula tip from an insertion path in the patient body which cannot be visually, whereby the insertion path is closely predetermined through the direction of the ultrasonic beam of the single oscillator pursuant to the resultant locating of a vessel. In the subject matter of the invention, having a plurality of oscillators which are to be sequentially excited, however, the ultrasound scanning beam constantly changes the incident beam location at a constant remaining beam direction. Introducing location, as well as introducing direction for the puncturing cannula or needle are thereby not predeterminable through location, respectively, direction of the incidence of an ultrasonic beam; these are obtained exclusively at a suitably located applicator from the relative position between the instantaneous location of the application-sided slot opening and the current postion of the aimed at puncturing point in the tissue, detectable through visual control. Since the relative position suitably pivots, correspondingly introducing or injecting direction or path of the puncturing cannula must be freely selectable for also a fixedly positioned applicator. Applicators with circular bores permit only a single introducing direction for a predetermined introducing location. They are therefore not suitable for the present inventive instance of application, meaning puncturing under visual control pursuant to a B-scan.

BRIEF DESCRIPTION OF THE DRAWINGS

Further advantages and details of the invention may now be ascertained from the following description of an exemplary embodiment thereof, taken in conjunction with the accompanying drawings; in which:

FIG. 1 shows a perspective view of an ultrasound applicator which is constructed pursuant to the invention; and FIG. 2 is a longitudinal sectional view of the applicator taken along line II—II of FIG. 1.

DETAILED DESCRIPTION

Illustrated in FIG. 1 of the drawings, shown supported on the application-sided surface 1 of a support member or carrier portion 2 are a plurality of small ultrasound transducer elements 3, and which are located adjacent each other in a single row. The carrier portion 2 thereby evinces an elongate rectangular configuration and preferably consists of a hardened plastic material which is provided with additions or inserts of heavy metals. The rectangle has a length of about maximum 200 mm, a height of about 30 mm, as well as a width of about 20 mm. The number of the transducer elements 3 which are positioned on the application side lie in a magnitude of about one hundred.

The transducer elements preferably consist of barium titanate or lead zirconate. The maximum width of each transducer element consists of about 1.3 mm, and the spacing between the individual elements within the row is about 0.2 mm. A common cable connector 4 connects the individual transducer elements 3 with an electrical transmitter-and receiver component (not shown), as well as with the echo recording tubes in the ulrasonic-echo planigraphic imaging apparatus.

The carrier portion 1, furthermore, is provided interiorly thereof with a slot 5 which extends across the transducer row in the longitudinal direction of the latter. The slot 5 is so shaped that is reduces from a predetermined maximum slot length 6 at the surface 7 which is remote from or opposite to the application side 1 of the carrier portion 2, towards a minimum slot length 8 at the application surface 1. The reduction is hereby effectuated conically towards both sides of a symmetrical axis 9 (shown in phantom lines) extending perpendicular to the application surface of the carrier portion. The cone aperture angle α at the cone tip, at the given maximum carrier portions dimensions, comprises about 40°. At an application sided slot length 8 of about 2 mm, and a carrier portion height of about 30 mm, the maximum slot length 6 at the surface 7 opposite to the application surface of the carrier portion 2 is about 22 mm. At the location of the slot opening 8 terminating centrally in the transducer row, the transducer row is provided with a gap or void of a total of two transducer elements.

The slot 5 serves as a guide slot for (metallic) puncturing cannulas or needles, for example, a puncturing cannula 10 according to FIG. 2 (shown in a perpendicular, as well as in a maximum oblique position). The diameter of usual cannulas consists of about 0.8 to a maximum of about 1.6 mm. It is thereby recommended that the slot width be selected at a value which is only slightly larger than the maximum occurring cannula diameters, for example, up to about 2 mm (for extremely thin cannulas, when required for correlation with the slot width, a sterilized reduction sleeve may be inserted). The slot width affords a satisfactory guidance to the puncturing cannula 10 into the body sectional plane which is scanned linewise by the ultrasonic beam of the transducer elements 3 (for example, sectional plane 11 of a body part 12 according to FIG. 2). The sectional plane thus represents that region of the body within the ultrasonic scanning region or field of transducer elements 3.

The utilization of the ultrasound applicator according to FIGS. 1 and 2 is effected as follows:

At the beginning of the examination, the applicator 2, 3 with the application surface containing the transducer row is applied to the body surface of a body 12 which is to be scanned. At a rapid sequential excitation of the individual transducer elements 3, as well as corresponding displacement of the applicator, a sectional surface 11 in the body which is suitable for puncture is selected, and through echo recording is rendered visiblle on the viewing apparatus of the ultrasound-echo planigraphic imaging apparatus as a corresponding section surface. For puncturing, the puncturing cannula 10 is then subsequently inserted into the slot 5 of the carrier portion 2 of the ultrasound applicator, and through displacement within the slot there is envisioned the desired puncturing point. Subsequently, the cannula 10, under constant visual control at the viewing apparatus, is pushed into the tissue of the body 12 in the direction toward the envisioned point.

Although the invention has been described with reference to a single row of ultrasound transducer elements being provided in the carrier portion, it is readily apparent that two or more rows may be provided, each row having a guide slot associated therewidth.

While there has been shown what is considered to be the preferred embodiment of the invention, it will be obvious that modifications may be made which come within the scope of the disclosure of the specification.

What is claimed is:

1. In an ultrasound applicator for ultrasonic-echo planigraphic imaging apparatus, said applicator including a carrier portion having an application surface adapted to be located on the body surface of a patent; and a plurality of ultrasound transducer elements mounted on said application surface in at least one row, the improvement comprising: said carrier portion including a guide slot for a puncturing cannula extending across said row of transducer elements in the longitudinal direction thereof, said guide slot reducing from a predetermined maximum slot length at the surface of said carrier portion opposite to said application surface to a minimum slot length at said application surface, said guide slot terminating in the application surface of said carrier portion in the center of said row of transducer elements, said row of transducer elements having a void of at least one transducer element at the location where said guide slot terminates in said application surface said transducer elements each having a maximum width of about 1.3 mm, a spacing of about 0.2 mm maximum between the individual transducer elements of a row of transducer elements and a slot length of about 2 mm at the application surface, and said row of transducer elements having a center void of a total of two transducer elements.

2. An ultrasound applicator as claimed in claim 1, said carrier portion being rectangular and having a length of about 200 mm maximum and a height of about 30 mm maximum, including about one hundred of said transducer elements, said guide slot having a minimum slot length of about 2 mm at said application surface and a maximum slot length of about 22 mm at the surface opposite thereto.

3. In a ultrasound applicator for ultrasonic-echo planigraphic imaging apparatus, said applicator including a carrier portion having an application surface adapted to be located on the body surface of a patient; and a plurality of ultrasound transducer elements mounted on said application surface in at least one row, the improvement comprising: said carrier portion including a guide slot for a puncturing cannula extending across said row of transducer elements in the longitudinal direction thereof, said guide slot reducing from a predetermined maximum slot length at the surface of said carrier portion opposite to said application surface to a minimum slot length at said application surface, said guide slot having a constant width, and said guide slot being slightly wider than the maximum diameter of commmon puncturing cannulas, and having a slot width of a value within a range from slightly greater than about 1.6 mm up to about 2 mm.

4. An ultrasound applicator as claimed in claim 3, said guide slot reducing conically on both sides of an axis of symmetry extending perpendicular to the application surface of said carrier portion.

5. An ultrasound applicator as claimed in claim 4, said guide slot forming an aperture in said application surface having an aperture angle of about 40° at the cone tip.

6. An ultrasound applicator as claimed in claim 4, said guide slot having a slot opening at the application surface of said carrier portion with a longitudinal extent not greater than about 2 mm.

7. An ultrasound applicator as claimed in claim 6, said row of transducer elements including transducer elements closely longitudinally adjacent the opposite ends of said slot opening at said application surface.

8. In an ultrasouond applicator for ultrasonic-echo planigraphic imaging apparatus, said including a carrier portion having an application surface adapted to be located on the body surface of a patient; and a plurality of ultrasound transducer elements mounted on said application surface in at least one row, the improvement comprising: said carrier portion including a guide slot for a puncturing cannula extending across said row of transducer elements in the longitudinal direction thereof, said guide slot reducing from a predetermined maximum slot length at the surface of said carrier portion opposite to said application surface to a minimum slot length at said application surface, said guide slot being open throughout a region on both longitudinal sides of an axis of symmetry extending perpendicular to the application surface of said carrier portion, and over the entire extent of the region between a slot opening of said maximum slot length at the surface opposite said application surface and a slot opening of said minimum slot length at said application surface, the walls of said guide slot accommodating a puncturing cannula extending through said guide slot at any angle over a range of angular positions on both longitudinal sides of the axis of symmetry of the guide slot, all such angular positions lying in a plane which intersects the row of transducer elements in the longitudinal direction thereof, and the lateral walls of said guide slot being disposed to constrain the path of a puncturing cannula as it is projected through said guide slot to lie within the scanning ultrasonic field of said row transducer elements regardless of the angular position of the cannula within said range.

9. An ultrasound applicator as claimed in claim 8, said guide slot accommodating a range of angular positions of about 40°.

10. An ultrasound applicator as claimed in claim 8, the slot opening at the application surface of said carrier portion having a lateral extent of not greater than about 2 mm.

11. An ultrasound applicator as claimed in claim 8, said row of transducer elements including adjacent transducer elements closely longitudinally adjacent the location where said guide slot terminates at said application surface, and the lateral extent of the slot opening at said application surface being substantially less than the corresponding lateral dimension of said adjacent transducer elements so that the guide slot guides a puncturing cannula into the path of the ultrasonic energy of one of the adjacent transducer elements as the cannula is projected beyond said slot at an angle to said symmetry axis within said range.

12. In an ultrasound applicator for ultrasonic-echo planigraphic imaging apparatus, said applicator including a carrier portion having an application surface adapted to be located at the body surface of a patient; and a plurality of ultrasound transducer elements mounted on said application surface in at least one row; said carrier portion including a guide slot for a puncturing cannula extending across said row of transducer elements in the longitudinal direction thereof, said guide slot reducing from a predetermined maximum slot length at the surface of said carrier portion opposite to said application surface to a restricted slot length at said application surface, and said carrier portion having means comprising said slot for receiving a puncturing cannula of given size and providing for angular adjustment of a puncturing cannula of such size over a range of angular positions substantially corresponding to said predetermined maximum slot length while essentially providing a fixed non-adjustable lateral constraint with respect to a puncturing cannula of such size extending through said slot in each angular position thereof over said range of angular postions, said means serving to guide a puncturing cannula of such size into a scanning region of said row of ultrasound transducer elements regardless of the angular position of the cannula in said slot.

* * * * *